(12) United States Patent
Haguet et al.

(10) Patent No.: US 9,256,008 B2
(45) Date of Patent: Feb. 9, 2016

(54) IMAGING SYSTEM COMPRISING MICROLENSES AND ASSOCIATED DEVICE FOR DETECTING A SAMPLE

(75) Inventors: Vincent Haguet, Grenoble (FR);
Marion Gabriel, Grenoble (FR);
François Chatelain, Beaulieu (FR);
Nathalie Picolletd'Hahan, La Ferriere (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 13/376,129

(22) PCT Filed: Jun. 2, 2010

(86) PCT No.: PCT/FR2010/051076
§ 371 (c)(1),
(2), (4) Date: Feb. 21, 2012

(87) PCT Pub. No.: WO2010/139900
PCT Pub. Date: Dec. 9, 2010

(65) Prior Publication Data
US 2012/0142086 A1 Jun. 7, 2012

(30) Foreign Application Priority Data
Jun. 2, 2009 (FR) ...................................... 09 53631

(51) Int. Cl.
*C12M 1/34* (2006.01)
*G01N 21/64* (2006.01)
(Continued)

(52) U.S. Cl.
CPC .......... *G02B 3/0056* (2013.01); *G01N 21/6456* (2013.01); *G02B 21/0008* (2013.01)

(58) Field of Classification Search
None
See application file for complete search history.

(56) References Cited

U.S. PATENT DOCUMENTS 5,694,478 A * 12/1997 Braier et al. .................. 382/133
7,427,742 B2 * 9/2008 Drowley et al. .......... G06T 9/00
250/208.1
(Continued)

FOREIGN PATENT DOCUMENTS

EP 1143016 10/2001
FO 2812943 2/2002
(Continued)

OTHER PUBLICATIONS

Int'l Search Report & Written Opinion issued in app. No. PCT/FR2010/051076 (2010).

*Primary Examiner* — Jill Warden
*Assistant Examiner* — Julie Tavares
(74) *Attorney, Agent, or Firm* — Knobbe, Martens, Olson & Bear, LLP

(57) ABSTRACT

The invention relates to an imaging system and an associated device for detecting a sample (4). The imaging system comprises a matrix (24) of photosensors (26), a first lamina (28) disposed opposite the matrix (24) of photosensors defining a face (28A) for supporting the sample, and a set (30) of optical elements, disposed between the matrix (24) of photosensors and the first lamina (28). Each microlens (34) is disposed above a photosensor (26) of the matrix (24) of photosensors. The set (30) of optical elements comprises a matrix (32) of microlenses (34). The set (30) of optical elements comprises an optical medium (36) disposed between the matrix (32) of microlenses and the first lamina (28), the refractive index of the optical medium (36) being substantially between 1 and the refractive index of the microlenses (34). The distance between the face supporting the sample (28A) and the apex of the microlenses (34) is substantially between 0 and 1500 μm as measured along the optical axis (Z) of the photosensors (26).

19 Claims, 6 Drawing Sheets

Figure 1:
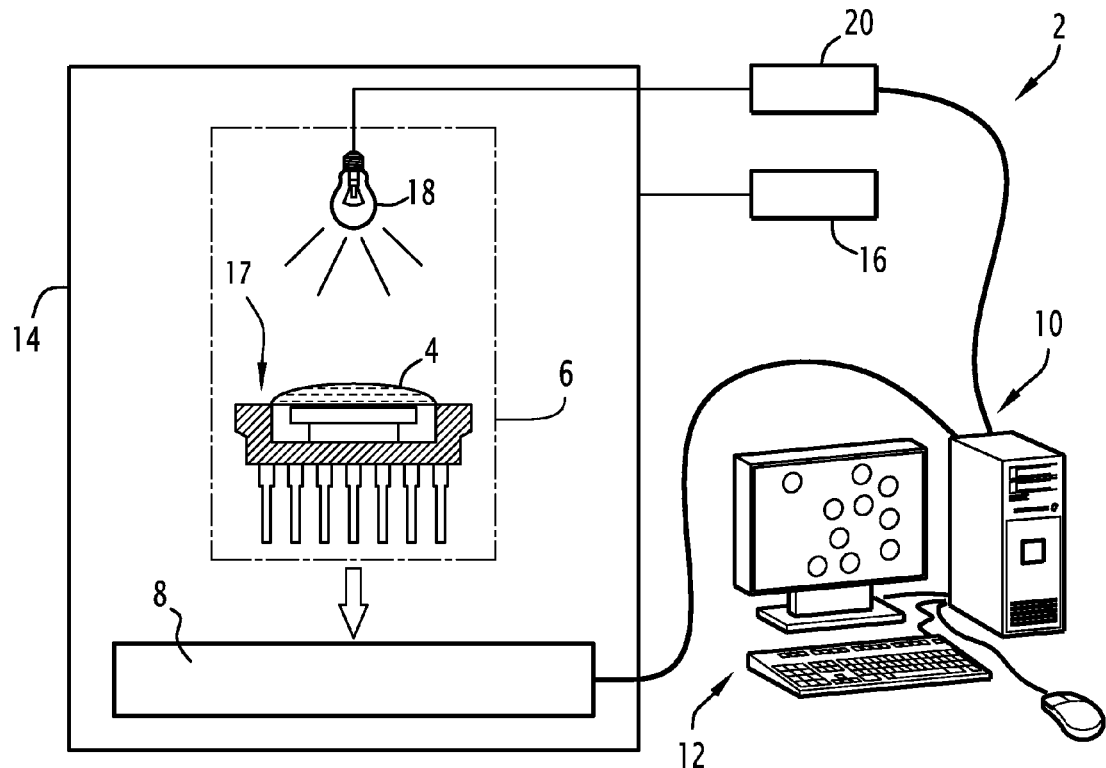

(51) Int. Cl.
  *H01L 27/146* (2006.01)
  *G02B 3/00* (2006.01)
  *G02B 21/00* (2006.01)

(56) References Cited

U.S. PATENT DOCUMENTS

2002/0182111 A1* 12/2002 Feygin ................ 422/82.05

2005/0046847 A1 3/2005 Cromwell et al.
2005/0237524 A1 10/2005 Kamei et al.

FOREIGN PATENT DOCUMENTS

| FR | 2812943 A1 * | 2/2002 |
| WO | WO 01/03833 | 1/2001 |
| WO | WO 0103833 A1 * | 1/2001 |

* cited by examiner

IMAGING SYSTEM COMPRISING MICROLENSES AND ASSOCIATED DEVICE FOR DETECTING A SAMPLE

CROSS REFERENCE TO RELATED APPLICATIONS

This application is a U.S. nationalization under 35 U.S.C. §371 of International Application No. PCT/FR2010/051076, filed Jun. 2, 2010, which claims priority to French application no. FR0953631, filed Jun. 2, 2009. The disclosures set forth in the referenced applications are incorporated herein by reference in their entireties.

The present invention relates to an imaging system comprising microlenses and an associated device for the detection and optical characterization of a sample.

The invention relates to the field of miniaturizing measuring instruments for chemical or biological analysis.

In biology, cell observation generally requires the use of an optical microscope in order to magnify the image of the cells and separate the details of that image. Similar equipment is used to view other types of biological objects, such as bacteria, yeasts, fungi, pollens, algae, liposomes, as well as synthetic particles. To that end, a microscope includes optical lenses (objective, eyepiece), a light source and at least one photo sensor. The microscopes used daily by researchers are often expensive and restrictive, in particular due to their spatial bulk. Generally, they do not make it possible to produce images continuously over time or at predefined moments.

One of the miniaturization routes currently considered is to eliminate the magnification lenses of the microscope and produce the image of the shadow or the diffraction pattern created on the sensitive surface of the photo sensors. The image formed by the shadow or diffraction pattern of the observed object in contact with the photo sensors is called photogram. A priori the resolution, defined as the capacity to distinguish two very close disks, is in this type system limited by the size of the pixels and the distance between the object and surface of the optical sensor. In a traditional microscope, it is limited by the diffraction in the lens system of the objectives.

Systems exist describing a system for imaging a sample comprising a matrix of photosensors, a first lamina disposed opposite the matrix of photosensors defining a face for supporting the sample, and a set of optical elements, disposed between the matrix of photosensors and the first lamina, the set of optical elements comprising a matrix of microlenses, a microlens (34) being situated above each photosensor (26) of the matrix (24) of photosensors.

However, the images acquired by such an imaging system do not show the morphology or the shape in the cases where the cells of the sample to be analyzed are adhesive. In fact, the suspended or adhered cells do not correspond to the same challenge: cells are objects having a low contrast with the culture medium because the optical indices are similar. When they are adhered, they have a flat and elongate shape, which makes them more difficult to image.

The aim of the invention is to propose a smaller device able to image cells, in particular adhesive cells, to locate and identify the cells, number them and analyze their morphology. The smaller size of the device makes it possible to insert it directly into an incubator in order to allow the proliferation of the cells of the sample.

To that end, the invention relates to a system for imaging a sample of the aforementioned type, characterized in that the set of optical elements comprises an optical medium disposed between the matrix of microlenses and the first lamina, the refractive index of the optical medium being substantially between 1 and the refractive index of the microlenses, and in that the distance measured along the optical axis of the photosensors between the face supporting the sample and the apex of the microlenses is substantially between 0 and 1500 μm.

According to specific embodiments, the system for imaging a sample includes one or more of the following features:
- the distance measured along the optical axis of the photosensors between the support face of the sample and the apex of the microlenses is smaller than or equal to $-150 \times F \times n + 400 \times F$, where F is the focal length of the microlenses measured in the air and n the refractive index of the optical medium and in that the refractive index of the optical medium is substantially between 1 and 1.64;
- it comprises a light source intended to light the sample, the light source being disposed above the sample so as to produce a transmission image;
- it comprises a light source intended to light the sample, the light source being disposed so as to light in the first lamina of the imaging system perpendicular to the optical axis of the imaging system;
- the light source can light with a wavelength comprised between 200 nm and 800 nm;
- the light source is a white light;
- the optical medium is a liquid;
- the imaging system comprises a cuvette containing the liquid and the sample;
- it comprises a second lamina disposed so that the sample is situated between the first lamina and the second lamina;
- the support face of the sample of the first lamina is disposed opposite the matrix of photosensors;
- the first lamina includes a slide and a removable lamina alongside the slide and defining the support face of the sample;
- the imaging system comprises means for adjusting the distance, measured along the optical axis of the photosensors between the support surface of the sample and the apex of the microlenses;
- the first lamina comprises a plurality of microchambers or microchannels;
- the photosensors can detect a light emitted between 200 nm and 800 nm by bioluminescence, chemiluminescence or fluorescence;
- the sample comprises cells and the photosensors associated with the microlenses are arranged so that a cell is covered by at least two adjacent photosensors in a first direction and two other adjacent photosensors in a second direction perpendicular to the first direction;
- the opening diameter of each microlens is at least two times smaller than the smallest lateral dimension of a cell and in that the distance between the optical axes of two closer neighboring microlenses is smaller than at least 30% of the opening diameter of a microlens, the opening diameter of a microlens being the diameter of the intersection section of the flat diopter and the convex diopter forming the microlens, and the smallest lateral dimension of a cell being the smallest dimension of the cell passing through the center of gravity thereof and measured in a plane parallel to the support face (28A) of the sample; and
- the opening diameter of each microlens is substantially comprised between 0.7 and 10 μm.

Thus, this smaller imaging system can produce cell images continuously over time or at predefined times to quantify the proliferation of the cells, individually monitor their movement and deduce their trajectory and speed therefrom, detect the divisions of the cells and establish relationships, show and quantify changes in morphology, identify cellular events of interest (rare events, etc.).

The invention also relates to a device for detecting and characterizing a sample characterized in that it comprises an imaging system as described above, an electronic controller and a computer system intended to control the imaging system.

According to specific embodiments, the device for detecting and characterizing a sample includes one or more of the following features:
- it comprises at least two imaging systems as described above according to the invention and steered in parallel by the electronic controller;
- the first lamina is shared by at least two adjacent imaging systems; and
- it comprises an incubation chamber in which the imaging system and the sample are placed.

Figure 2:
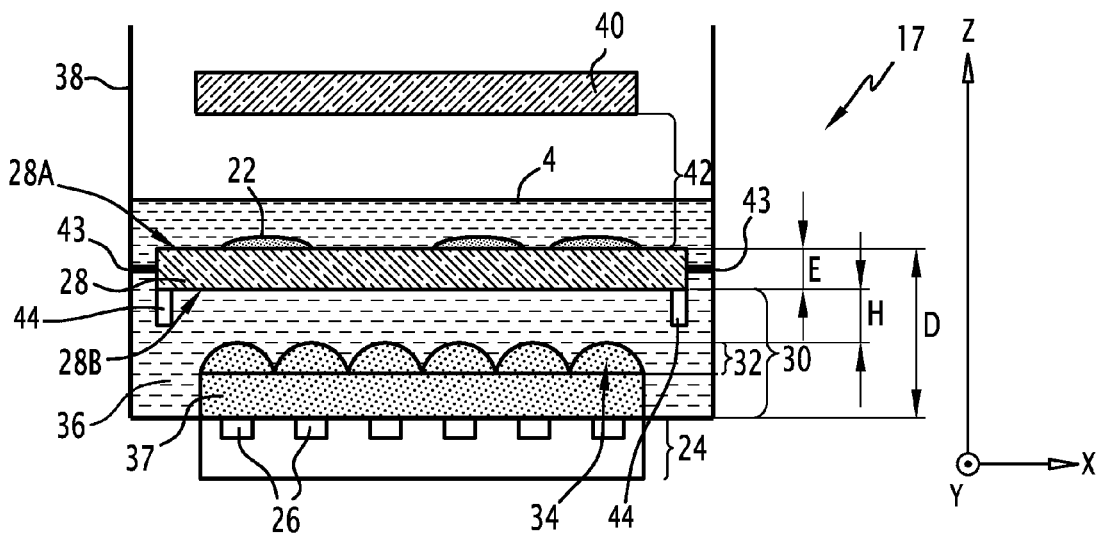
Figure 3:
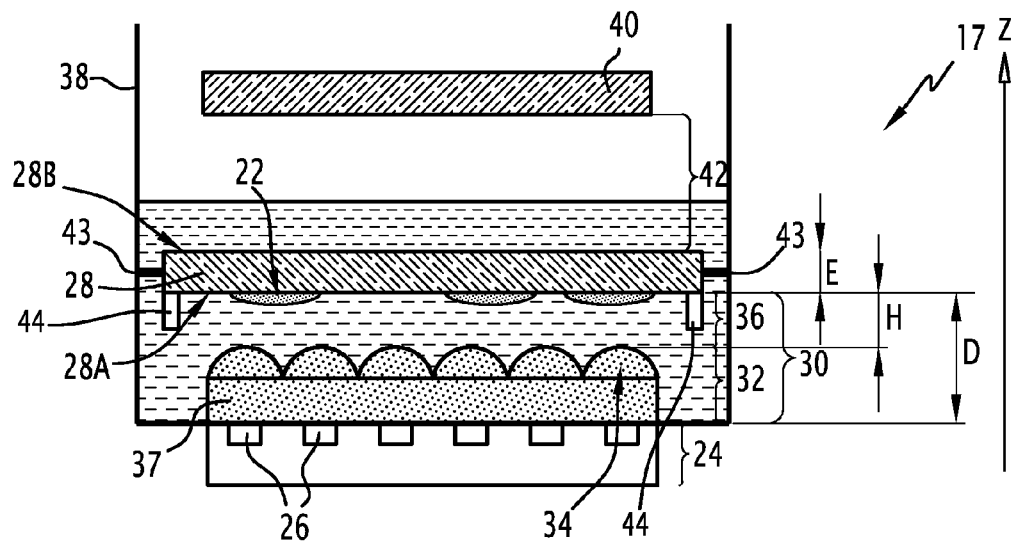
Figure 4:
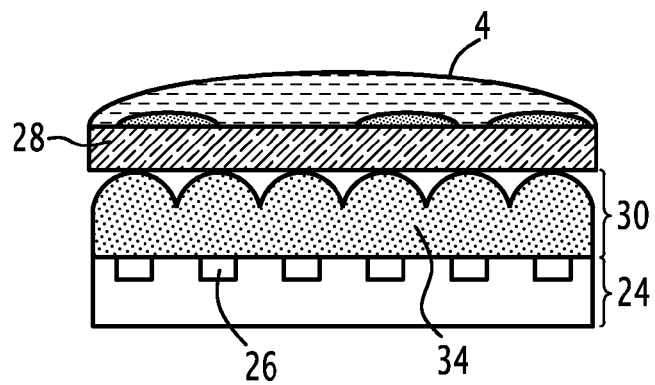
Figure 5:
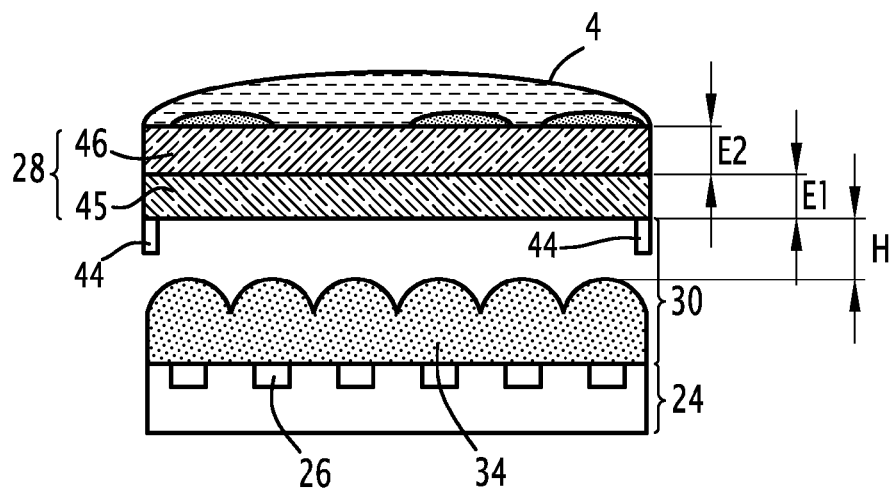
Figure 6:
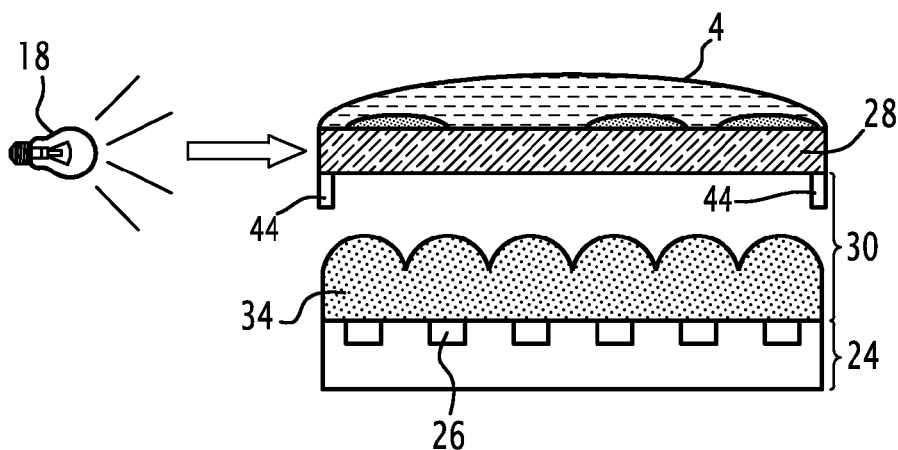
Figure 7:
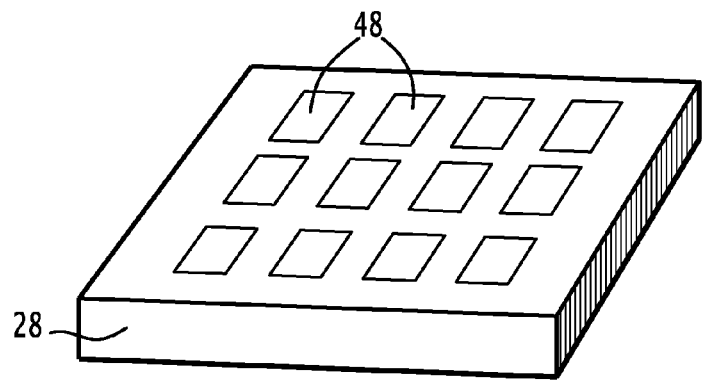
Figure 8:
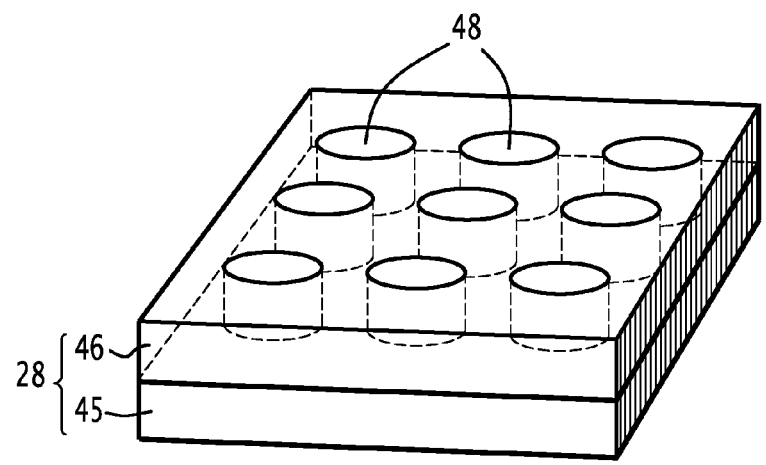
Figure 9:
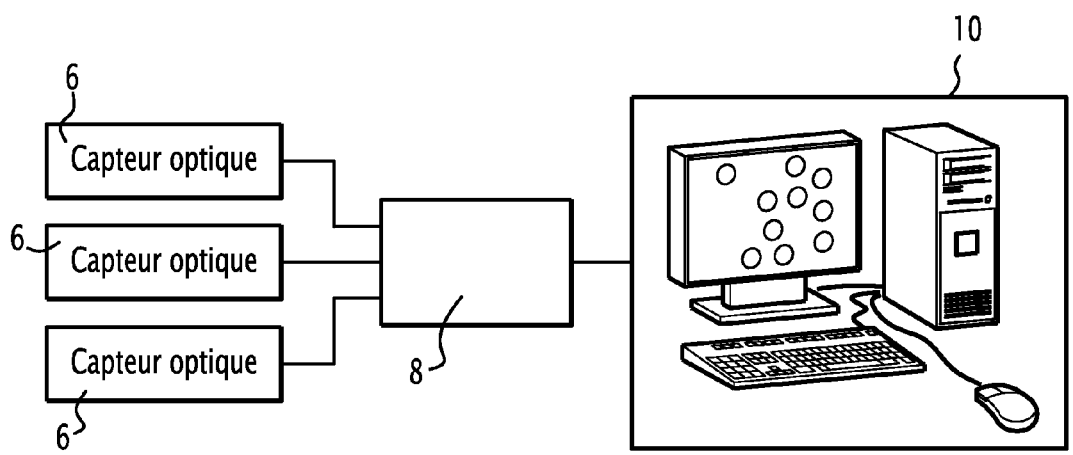
Figure 10:
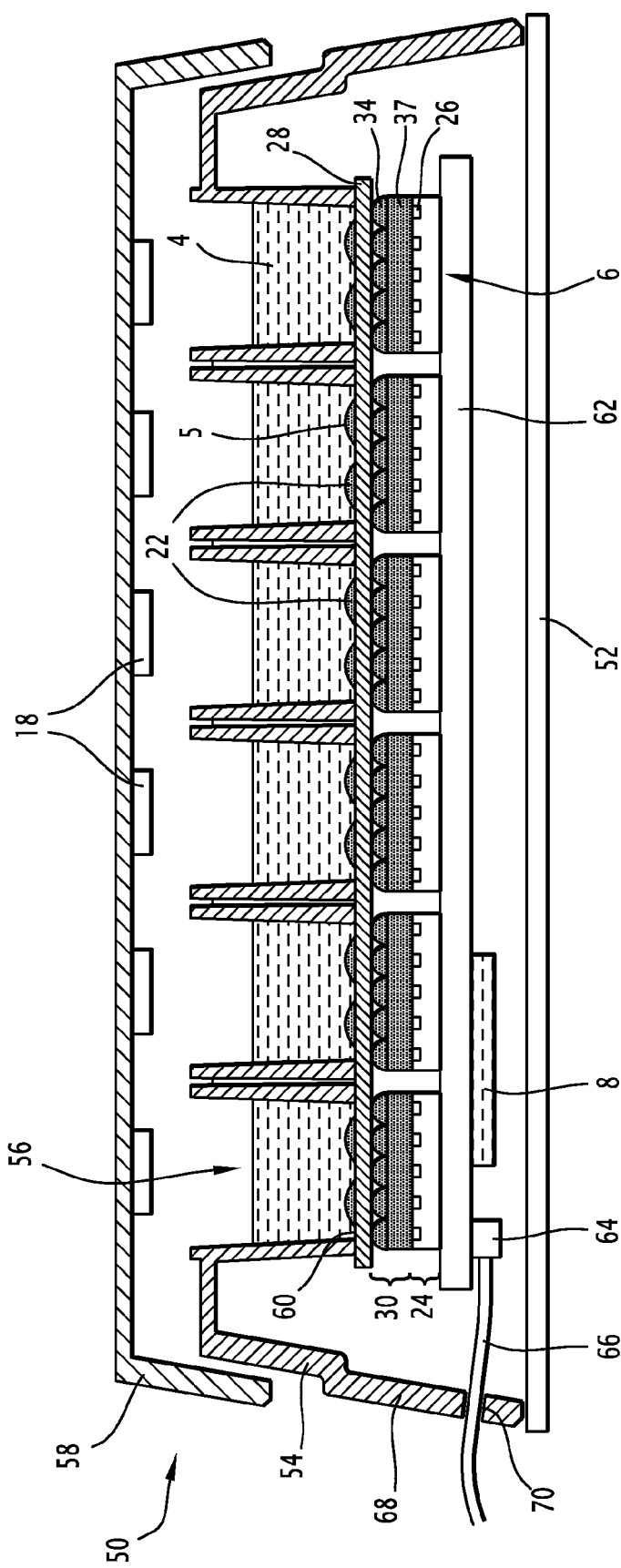
Figure 11:
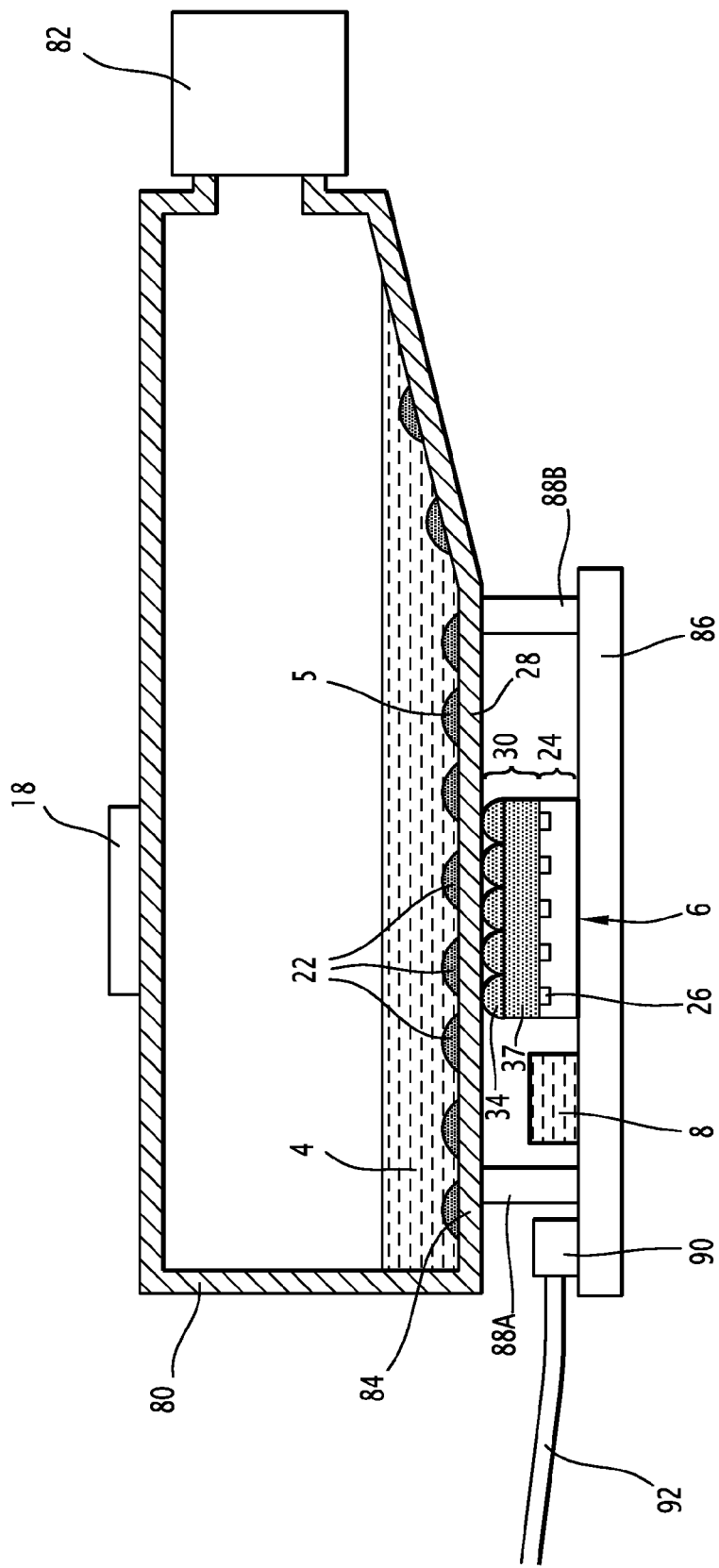

The invention will be better understood upon reading the following description, provided solely as an example, and done in reference to the appended drawings, in which:

FIG. 1 is a diagrammatic view of a device for detecting and characterizing a sample according to the invention, FIG. 2 is a diagrammatic view in cross-section of an optical system of an imaging system adapted to detect and characterize a sample according to the invention, FIGS. 3, 4 and 5 are views identical to that of FIG. 2 of different embodiments of an optical system of an imaging system according to the invention, FIG. 6 is a diagrammatic view of another embodiment of an imaging system according to the invention, FIGS. 7 and 8 are diagrammatic views of a lamina incorporated into an optical system of an imaging system and including a microfluidic system according to the invention, and FIGS. 9, 10 and 11 are diagrammatic views of three other embodiments of a device for detecting and characterizing one or more samples according to the invention.

Figure 12:
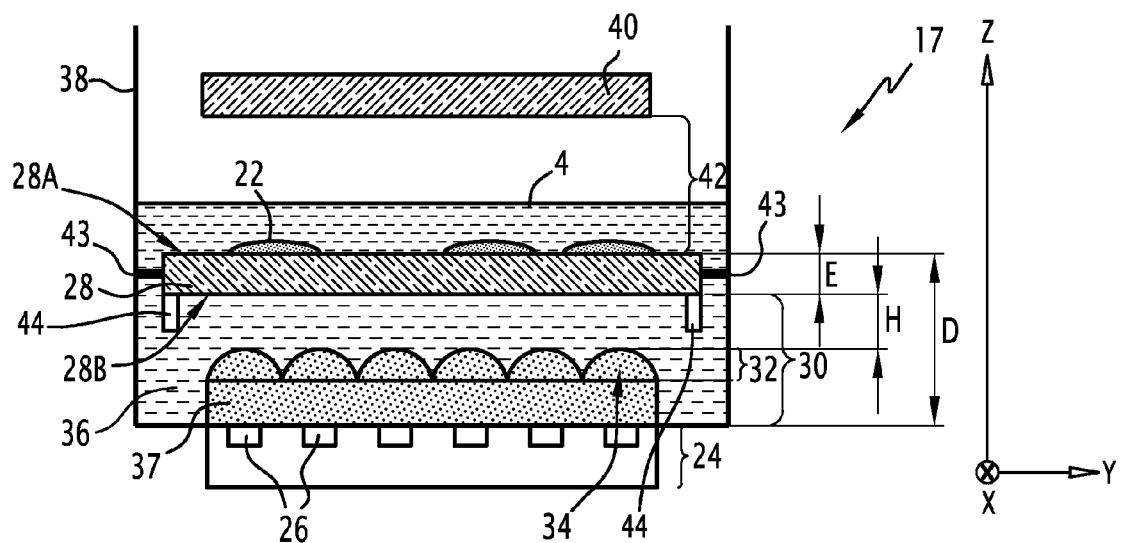

FIG. 12 is a diagrammatic view in cross-section of the optical system of FIG. 2, the cross-section plane of FIG. 12 being perpendicular to the cross-section plane of FIG. 2.

The invention relates to a device 2 for detecting and characterizing a sample 4, one embodiment of which is illustrated in FIG. 1. The sample 4 comprises objects 5 to be detected and imaged in order to study their characteristics (morphology, size, etc.). The objects 5 are micrometric-sized objects (bacteria, yeasts, fungi, pollens, algae, liposomes, etc.) and preferably cells.

The device 2 comprises at least one imaging system 6 intended to detect and characterize the sample 4 and an electronic controller 8 able to control the imaging system 6. The electronic controller 8 comprises a support able to fix the imaging system 6, for example to plug it in if it comprises connection plugs.

The imaging system 6 is described in detail hereafter.

The device 2 also includes a computer system 10 intended to steer the electronic controller 8 to which it is connected.

The computer system 10 comprises a man/machine interface 12 intended to enter information to steer the electronic controller 8 and display information concerning the sample 4.

The computer system 10 also includes a computation unit able to perform processing on the images and a storage unit to record the acquired images of the sample.

The device 2 comprises an incubation chamber or incubator 14 and means 16 for monitoring and regulating the $CO_2$ level, humidity and temperature inside the incubation chamber. For example, the incubator 14 is a standard incubator for cellular biology, with dimensions in the vicinity of one cubic meter in a known manner, which may potentially contain several imaging systems 6, or an incubator miniaturized to the dimensions of an imaging system 6. In the latter case, the device 2 is easily transportable to be used, for example, near a sample collection site.

The imaging system 6, the electronic controller 8 and the sample 4 are disposed inside the incubation chamber 14.

The imaging system 6 includes an optical system 17 intended to analyze the sample 4 and, preferably, the imaging system 6 includes at least one light source 18 intended to light the sample 4, the latter being arranged between the light source 18 and the optical system 17.

The light source 18 is situated opposite the optical system 17 so as to produce a transmission image of the sample and at a controlled distance, for example a distance of several centimeters. The light source 18 is situated at the vertical of the optical system 17.

According to one alternative, the light source 18 is offset relative to the vertical of the optical system 17, for example at a distance of several centimeters according to an arc of circle around the optical system 17.

Furthermore, the light source is slightly or not at all collimated with a critical light angle smaller than 20°, for example 10°.

Nevertheless, depending on the operator's needs and in a known manner, the light source can be collimated by a system of lenses, diaphragms and/or filters, directional or not, polychromatic or monochromatic, polarized or not, extended or periodic.

The light source 18 can light with a wavelength comprised between 200 nm and 800 nm, i.e. emitting in the visible and/or near ultraviolet (UV). Preferably, it is a white light, i.e. a light emitting a continuous wavelength spectrum, in particular in the visible region (400 nm to 800 nm).

For example, the light source 18 comprises a light-emitting diode (LED), for example a white LED, an array of LEDs, an incandescent bulb, or a light-emitting sheet or flat LED such as an XLamp marketed by Cree (Durham, United States).

According to one alternative, the light source 18 includes an illumination device of the Kölher type, i.e. an imaging system commonly used in optical microscopes to illuminate the object or sample.

A means 20 for controlling the light source 18 is incorporated into the device 2 and connected to the computer system 10.

According to one alternative, the light source 18 is positioned above the optical system 17 so that it lights the sample at a specific angle (lighting angle) monitored by the operator or by the computer system 10.

The light source 18 lights the object or sample at an intensity and/or during periods and/or at moments specified by the operator or computer system 10.

Depending on the operator's needs, the light source 18 can be shared by several samples or only light a single sample.

The operation of the device 2 for detecting and characterizing a sample 4 according to the invention will now be described.

In order to study and analyze the sample 4, an operator places it in the imaging system 6. The imaging system 6 is connected to the electronic controller 8, for example by plugging the optical system 17 onto the support of the electronic controller 8.

If necessary, the assembly comprising the optical system 17, the sample 4, the electronic controller 8 and the light source 18 is placed in the incubation chamber 14, in particular to allow the normal proliferation of the cellular population.

The incubator 14 regulates the temperature and $CO_2$ level, and maintains a high humidity level owing to the monitoring and regulation means 16 adjusted beforehand by the operator.

Furthermore, this assembly (imaging system 6 including the light source 18, sample 4 and electronic controller 8) is preferably placed in a darkroom in order to reduce parasitic noise related to the ambient light.

The operator then enters information via the man/machine interface 12 to adjust the or each light source 18 via the light control means 20 and to steer the optical system 17 of the imaging system 6 via the electronic controller 8. The operator thus checks remotely, using the computer system 10, the or each imaging system 6, including the or each light source 18.

During operation, the or each light source 18 lights the sample 4. The light or optical signal (photons) transmitted by the sample 4 is converted by the optical system 17 of the imaging system 6 into an electric signal. The electric signal is then transmitted by the electronic controller 8 to the computer system 10.

The data acquired by the optical system 17 of the imaging system 6 are recorded in the storage unit of the computer system 10. Then, the computation unit reconstructs the image or image sequence of the cells 5 of the sample 4 from the data. In fact, the device records, in a known manner, dynamic events, either by performing a continuous acquisition (video mode) to obtain a film, or by acquiring images at regular intervals (photo mode) to obtain a sequence of images, and not only the intensity of the optical signal detected during transmission of the sample.

Lastly, the operator controls, via the man/machine interface 12, the computation unit to perform other processing of the image or image sequence in order to characterize the sample 4. For example, the computation unit may spatially identify the cells 5 of the sample, identify the cells 5 based on an analysis of their morphology and/or fluorescent signals and/or specific luminescents, number the cells, compare their position with their earlier position, record the trajectory and speed of migration of each cell, quantify the proliferation of the cells, characterize the morphology of each cell (computation of the perimeter and area covered by each cell, circle symmetry criterion of each cell, texture of the contour), show morphological changes on individual cells or a population of cells, segment the image to trace the junctions between the cells and compute the number of neighboring cells, detect events of interest such as cellular divisions or differentiations or calcareous bursts, establish relationships, and/or locate organelles (nuclei, etc.) in the cells. Furthermore, it can eliminate background noise, for example by producing, for each experiment, an image with a light background (parasitic light) and with a dark background (dark current). It can also reconstitute films of the cellular culture on all or part of the image.

According to another embodiment for a sample 4 emitting light, for example a bioluminescence or a chemiluminescence, the device 2 is used without any light source 18. In that case, the analyses must be done in total darkness (in a darkroom). The intensity of the luminescence is integrated for a particular period by the operator in order to increase the sensitivity of the measurement, for example the integration time of the luminescence is 5 minutes.

FIG. 2 is a diagrammatic cross-sectional view of the optical system 17 of the imaging system 6 intended to detect and characterize the sample 4. For example, the sample 4 comprises objects, for example cells 5 and preferably adhered biological cells 22 in an aqueous medium, in a known manner a culture medium.

The optical system 17 of the imaging system 6 comprises a matrix 24 of photosensors 26, regularly arranged, whereof the photosensitive area of each photosensor 26 is for example made from silicon.

The optical system 17 also includes a first transparent lamina 28 disposed opposite the matrix 24 of photosensors 26 defining a support face 28A of the sample 4 support. The face 28A is preferably flat and transparent.

Preferably, the first lamina 28 has a specific surface treatment to capture and/or favor the adhesion of the cells 22 on the support face 28A of the sample 4, in a known manner through a functionalization method with appropriate proteins, preferably proteins of the extracellular matrix, for example fibronectin, or with an oxygen plasma.

Furthermore, another surface treatment prevents adhesion on the face 28B opposite the face 28A, support for the sample, for example by using polylysine-PEG (polylysine-polyethylene glycol), which gives it hydrophobic properties.

For example, the support face 28A of the adhered cells 22 has a surface treatment to increase the adhesion of the cells thereon and the other face 28B has a surface treatment to reduce or eliminate the adhesion of the cells 22.

For example, the first lamina 28 serves as support for the cellular culture.

The first lamina 28 has good qualities in terms of optical transmission, for example it is made from glass or polystyrene.

The optical system 17 of the imaging system 6 also comprises a set 30 of optical elements disposed between the matrix 24 of photosensors 26 and the first lamina 28.

The set 30 of optical elements includes a separator element 37 situated opposite and in contact with the matrix 24 of photosensors, and a matrix 32 of microlenses 34 disposed between the separator element 37 and the first lamina 28.

The matrix 32 of microlenses 34 is positioned above the matrix 24 of photosensors 26 so that a microlens is situated above each photosensor 26 of the matrix 24 of photosensors. Thus, each microlens 34 is associated with a photosensor 26. The optical axis of each microlens 34 is substantially combined with the optical axis of a photosensor 26.

For example, the optical axis of a microlens 34 and the optical axis of a photosensor 26 can be slightly offset, the offset (angular or in distance) being less than or equal to 20%. This offset is either involuntary as the result of a difficulty in aligning the microlens matrix with the photosensor matrix, or deliberate so as to reorient an oblique incident optical beam toward the photosensor owing to the microlens.

The separator element 37 is formed by one or more optically transparent materials, for example filters or passivation layers.

The function of the separator element is to space the matrix 24 of photosensors 26 away from the matrix 32 of microlenses 34 so that the light radii are concentrated or focused toward the photosensors.

The set 30 of optical elements also comprises a first medium 36, with refractive index or optical index n, disposed between the microlens matrix 32 and the first lamina 28. The first optical medium 36 is intended to modify the focal distance of each microlens 34. In fact, in the first medium 36, with optical index n, the focal distance of each microlens 34 is $$F_n = \frac{n_{lens} - n_{air}}{n_{lens} - n} \times F,$$

where F is the focal distance of each microlens 34 measured in the air.

The refractive index of the first optical medium 36 is substantially comprised between 1 and the refractive index of the microlenses 34. Preferably, the medium 36 is a gel or a liquid, for example an oil.

The optical system 17 of the imaging system 6 also includes a second lamina 40 disposed so that the cells 22 are situated between the first lamina 28 and the second lamina 40 in a second medium 42 delimited by the two laminas 28, 40.

Advantageously, the second lamina 40 has a surface treatment from among those already described for the first lamina 28.

The second medium 42 comprises a liquid, for example a biological liquid susceptible to cellular culture such as, traditionally, DMEM (Dulbecco's Modified Eagle's Medium) or a saline solution such as a phosphate buffered saline (PBS).

The level of the liquid of the second medium is such that it covers the support face 28A of the sample 4 and the objects 22.

According to one alternative, the first medium 36 is a liquid similar to that of the second medium 42.

The optical system 17 of the imaging system 6 comprises a tight cuvette 38 in which the matrix 30 of optical elements, the first lamina 28, and the sample 4 are placed so as to contain the liquids or gels of the first medium 36 and/or the second medium 42.

The bottom of the cuvette 38 can coincide with the surface of the photosensors 26. For example, the cuvette 38 is pierced at the bottom and adhered with the matrix 24 of photosensors 26 in order to guarantee sealing owing to a biocompatible glue.

The optical system 17 of the imaging system 6 also includes separating means 43 able to separate the first medium 36 from the second medium 42 if the two are different. This separating means 43 is fixed to the walls of the cuvette 38 or to the first lamina 28.

According to another alternative, the distance measured along the optical axis Z between the first slide 28 and the second slide 40 is adjusted so as to obtain, in a known manner, a configuration between slide and lamina of the sample 4. In this configuration the second lamina 40 is in contact with the sample 4.

The second lamina 40 can favor gaseous exchanges through the second lamina 40, and/or prevent evaporation through the second lamina 40 of part of the second medium 42, for example of the culture medium and the sample 4.

The optical system 17 also comprises means 44 for adjusting the distances measured along the optical axis Z between the support face 28A of the sample of the first lamina 28 and the face of the photosensors 26 disposed opposite the first lamina 28.

Preferably, this adjusting means 44 includes at least one piezoelectric ceramic. The adjusting means 44 can be mechanically fixed to the bottom or on the edges of the cuvette 38 or on the support of the matrix 24 of photosensors 26.

According to another alternative, the first lamina 28 is fixed at a fixed height to the walls of the cuvette 38 of the imaging system 6 by a mechanical, electrostatic, magnetic or equivalent means.

The first lamina 28, and therefore the sample 4 and the objects 5, preferably adhered cells 22, can be removed from the optical system 17 of the imaging system 6, depending on the operator's needs, for example for characterization of the sample on another instrument or for additional treatment of the sample (dying, marking with a fluorophore, etc.). The first lamina 28, and the sample or object, can also be repositioned in the imaging system 6.

The operation of the imaging system 6 according to the invention will now be described.

During the method for analyzing a sample by the device 2 described above, the manufacturer or operator of the imaging system chooses the separator element 37 and the first lamina 28 beforehand according to their optical characteristics (materials, refractive index, thickness, etc.) and the desired use/application.

Then, the matrix 32 of microlenses 34 is chosen taking into account the angle of the acceptance cone of the photosensors 26, which is controlled by the presence of the microlenses 34, in particular by the nature (refractive index) and shape (curve radius) of each microlens 34.

Each microlens 34 comprises a flat diopter and a convex diopter. The upper face opposite the sample of the microlenses is the convex diopter, which can be likened to a spherical bowl. Preferably, the microlenses are made from polystyrene, polyamide, AZ4562 photoresin or a similar material, poly(dimethylsiloxane), SU-8, silica, boron phosphorous silicate glass (BPSG), or a transparent thermoplastic material such as poly(methyl methacrylate) (PMMA) or polycarbonate.

The focal length of each microlens 34 is less than 25 μm, preferably less than 10 μm, so as to limit optical cross-talk phenomena between the microlenses and the underlying associated photosensors.

Preferably, the opening diameter of each microlens is at least two times smaller than the smallest lateral dimension of a cell. The smallest lateral dimension of a cell is the smallest dimension of the cell passing through its center of gravity and measured in a plane perpendicular to the optical axis of the imaging system, i.e. in a plane parallel to the face 28A of the lamina serving as support for the cell.

Moreover, the distance between the optical axes of two closer neighboring microlenses is preferably less than at least 30% of the opening diameter of a microlens. As a reminder, the opening diameter of a microlens is the diameter of the intersection section of the flat diopter and the convex diopter forming the microlenses.

The photosensors 26 associated with the microlens 34 are arranged so that an object 5, preferably a cell, is covered by at least two adjacent photosensors in a first direction and at least two other adjacent photosensors in a second direction perpendicular to the first direction.

Thus, the image of a cell is done by at least a 2×2 matrix of adjacent photosensors.

For example, the opening diameter of each microlens is substantially comprised between 0.7 and 10 μm, preferably between 0.7 and 3.0 μm, to image objects such as cells whereof the diameter is substantially between 20 and 30 μm. These values make it possible to avoid a discontinuity in the image of the objects, even until a same portion of the cell contributes to the light intensity of two neighboring photosensors. Over-sampling of the object 5 is preferable to under-sampling in order to produce good-quality images of the cells.

Each cell is thus shown in the image by at least 2 pixels per side, preferably by at least 6 pixels per side, so as to facilitate the subsequent computer processing on the images of the cells: the more the cells are represented by a large number of pixels, the more the contrast improvement, filtering and intensity thresholding operations carried out during the computer processing of the images will correspond to reality.

For example, the distance between the optical axes of two closer neighboring microlenses is less than 3.0 μm for microlenses with an opening diameter of 10 µm, less than 900 nm for microlenses with an opening diameter of 3.0 µm, less than 210 nm for microlenses with an opening diameter of 700 nm.

Then, the manufacturer or operator chooses the first medium 36 as a function of its refractive index n in order to modify the focal distance of the microlenses 34 and thus the acceptance angle of the photosensors 26. In fact, the light beams are deflected at the optical interface between the first optical medium 36 and each microlens 34 according to Descartes' law. Thus, the index of the first medium 36 also makes it possible to adjust the angle of the acceptance cone of the photosensors.

More specifically, the selection of the refractive index of the first medium 36 controls the position of the intersections of the acceptance cones of neighboring or adjacent photosensors. Thus, the angle of the acceptance cone of the photosensors 26 is increased, and consequently the position of the intersections of the acceptance cones of neighboring photosensors is decreased, by increasing the refractive index n of the medium 36, and vice versa.

For example, for a microlens 34 made from polystyrene with a refractive index 1.61, it suffices to replace the medium 36, initially air (i.e. n=1.0003), with an oil having a refractive index 1.55 to magnify the acceptance cone of the photosensors 26.

The refractive index of the first medium 36 is substantially comprised between 1 and the refractive index of the microlenses 34, preferably between 1 and 1.64.

In fact, any optically active material, situated between the matrix of photosensors and the sample, participates in modifying the acceptance cone of the photosensors. In particular, this is the case for the separator element 37 and the first lamina 28. For the latter, the light beams are deflected at the optical interface between the first lamina 28 and the first optical medium 36 according to Decartes' law. As a result, the choice of the first lamina also adjusts the acceptance cone of the photosensors. Nevertheless, it is also chosen for its optical qualities (high transmission) and is used as support for the objects 5 and preferably the adhered cells 22 to be imaged.

Then, owing to the adjustment means 44, the distance, measured along the optical axis Z, between the support face 28A of the sample 4 of the first lamina 28 and the apex of the microlenses 34, is adjusted, and consequently the thickness of the first medium 36 is as well. The distance is adjusted so as to be comprised between 0 and 1500 µm, and preferably between 100 and 500 µm.

Preferably, this distance is smaller than or equal to $-150 \times F \times n + 400 \times F$, where F is the focal distance of the microlenses 34 measured in the air and n is the refractive index of the first optical medium 36.

H denotes the distance measured along the optical axis Z, between the face of the first lamina 28 opposite the microlenses and the apex of the microlenses. Adjusting the distance H then makes it possible to obtain a more or less clear and/or more or less contrasted image of the cells 5, preferably of the cells 22 adhered to the sample 4 depending on what the operator wishes to observe as details of the cells 5.

In fact, varying the distance D between the object 5 and the surface of the photosensors results in:
- modifying the size or magnification of the image of the object, i.e. spreading over a variable number of adjacent photosensors: the further the object is from the matrix 24 of photosensors 26, the more it is imaged by a large number of photosensors 26, and thus the larger the object appears on the final image produced,
- showing the diffracted contour of the object 5, preferably an adhered cell 22, from a certain height. Close to the surface, the diffraction pattern on the contour of the object is not shown because the diffraction pattern is concentrated on a single photosensor, which does not make it possible to reveal the spatial details of the diffraction pattern. As one moves gradually further away from the surface, the diffraction pattern on the contour of the object spreads over 2, 3, 4, etc. adjacent photosensors and is better and better observed. Nevertheless, far from the surface, the diffraction pattern is diffused on too large a number of photosensors (it is then not possible to establish a usable image of the object if the image of a point of the object spreads over more than 200 photosensors), and
- modifying the contrast of the contour of the object.

The optical properties of the faces 28A and 28B of the first lamina 28 can be optimized to reinforce the diffraction, diffusion, interference and dispersion effects making it possible to view the contour of the cells 22.

In a second embodiment of the optical system 17 of the imaging system 6 illustrated in FIG. 3, the face 28A of the first lamina is situated opposite the matrix 24 of photosensors 26; the sample 4 comprising cells 5, preferably adhered 22 to the face 28A of the first lamina, is therefore disposed between the first lamina 28 and the matrix 32 of microlenses 34.

This embodiment makes it possible to do away with the thickness of the first lamina 28 in adjusting the distance between the objects to be imaged and the apex of the microlenses. This configuration has the advantage of offering very small, practically zero, distances between the objects 22 and the microlenses 34, and making images as close as possible to the photosensors 26.

According to a third embodiment shown in FIG. 4, the first lamina 28 is placed on the apex of the microlenses 34. The distance H between the apex of the microlenses and the face 28B opposite the microlenses of the first lamina 28 is then zero.

In that case, adjusting the distance between the support face 28A of the sample and the apex of the microlenses amounts to choosing a thickness E of the first lamina 28, adapted so that the measured distance, along the optical axis Z of the photosensors 26, between the support face of the sample 28A and the apex of the microlenses 34, is substantially comprised between 0 and 1500 µm, and preferably between 100 and 500 µm.

Nevertheless, it must be noted that the first medium 36 is still present in the interstices between the microlenses 34 and the first lamina 28, and consequently still acts on the acceptance cones of the photosensors 26.

According to a fourth embodiment shown in FIG. 5, the first lamina 28 includes a slide 45, with thickness E1, and a removable lamina 46, with thickness E2, alongside the slide 45 and defining the support face for the sample; the sum of the thicknesses E1 and E2 is consequently equal to the thickness E of the first lamina 28. This alternative makes it easier to move the sample without altering the distance H between the first lamina 28 and the apex of the microlenses 34 previously adjusted.

The presence of the second lamina 40, for example made from glass, is especially necessary in the case of a use in fluorescence, for example to image fluorophores or quantum dots. In this embodiment, the first and second laminas 28, 40 are preferably optical filters.

Preferably for this use, the light source 18, then excitation source, is monochromatic.

The second filter 40 is not necessary if the excitation wavelength is filtered by the first filter 28. For example, by eliminating the second lamina 40 and using a first glass lamina 28 as filter, the absorbance of the glass in the ultraviolet (UV) filters the excitation light if it is in the UV. A second example consists of a first lamina 28 whereof the face 28A or the face 28B is covered with a filtering stack, made by stacking dielectric layers, which absorbs the excitation wavelength.

According to one alternative, the optical system 17 of the imaging system 6 comprises a filter, or an array of dedicated filters, situated between the matrix 24 of photosensors 26 and the matrix 32 of microlenses 34. For example, this filter, or array of filters, is integrated into the separator element 37. The filters can be different under adjacent microlenses in order to characterize a same sample 4 according to at least two different wavelengths.

According to another alternative, the second lamina 40 is a directional filter so as to compensate for the absence of a collimation system for the light source 18, which causes distortions in the image.

According to another embodiment illustrated in FIG. 6, the light source 18 is arranged so as to make the light pass into the first lamina 28 perpendicular to the optical axis Z so as to light the sample 4 or the objects 22 from inside the lamina.

According to another alternative, either one of the laminas 28, 40 is a polarizer, or both laminas 28, 40 are cross-polarizers. In the first case, the light source 18 emits rectilinearly polarized light. For example, the light source 18 is a liquid crystal display (LCD). In the second case, the light source 18 does not emit polarized excitation light, and the excitation light is then polarized by the second polarizer 40. In both cases, the excitation light is stopped by the first polarizer 28 while the fluorescent emission light coming from the sample 4 is polarized and transmitted by the first polarizer 28. The intensity is lower in this configuration, but the signal to noise ratio is increased relative to a direct transmission of the excitation light. Preferably, the second polarizer 40 is in direct contact with the liquid making up the second medium 42 to avoid depolarization of the excitation light at the air/liquid interface.

According to another embodiment illustrated in FIG. 7, the first lamina 28 comprises a plurality of microchambers (or wells) 48 that may or may not be in communication with one another. The microchambers 48 are preferably arranged in a matrix, for example the microchambers 48 are formed on or etched in the first lamina 28. The thickness E participating in adjusting the distance between the face 28A of the first lamina 28 and the apex of the microlenses 34 is then the distance measured along the optical axis Z between the bottom of the microchambers 48 and the face 28B of the first lamina 28.

According to the alternative illustrated in FIG. 8, the microchambers 48 are formed in the entire thickness E2 of the removable lamina 46 previously described, and the thickness participating in adjusting the distance H between the face 28B of the first lamina 28 and the apex of the microlenses 34 is then the thickness E1 of the slide 45.

According to one alternative, the plurality of microchambers 48 forms a plurality of flow areas or microchannels for the sample, intended to circulate a fluid, for example the sample 4, using means for actuating the fluid incorporated into the optical system 17 of the imaging system 6. In a known manner, the actuating means are micropumps, microvalves, etc.

The plurality of microchambers 48 or microchannels is used, for example to perform screening by parallelizing observations on the same optical system 17 of the imaging system 6. In a known manner, parallel observations make it possible to reproduce experiments, study several cell types and/or several cell densities, vary the spatial organization, reagent concentrations, culture conditions, etc.

One then records the optical signal coming from each microchamber 48 or microchannel in order to reconstruct the image of each microchamber 48 or microchannel.

Advantageously, the images of each microchamber 48 or microchannel correspond to the entire lower surface of each well or study area 48 contrary to the observations done in traditional optical microscopy transmission.

Another embodiment intended to perform parallel studies is shown in FIG. 9; the device then comprises a plurality of imaging systems 6 steered in parallel by a same electronic controller 8. In that case, the computer system 10 manages the signals coming from each imaging system 6 in a synchronized or alternating manner.

According to one alternative, the device comprises a plurality of imaging systems 6 steered in parallel by several electronic controllers 8. Using a limited number of electronic controllers 8 makes it possible to centralize the interface function between the imaging systems according to the invention and the computer system 10.

Preferably, the imaging systems 6 are mounted on a same electronic circuit 8 and/or assembled in a housing or on a rack, in order to simplify handling by the operator and limit the space taken up by the device 2 in the incubator 14.

According to two embodiments illustrated in FIGS. 10 and 11, the first lamina 28 is respectively the bottom of a well plate or the wall of a bottle intended for cell cultivation.

Advantageously, the walls of the well plates (or microplate) and bottles for cell cultivation are sterile and have a surface treatment favoring the adhesion of the cells, for example a deposition of proteins of the extracellular matrix or an oxygen plasma. The sterility and the surface treatment improve the attachment, spread and growth of cells on these supports, in particular on the support surface 28A of the objects 5, preferably the adhered cells 22.

FIG. 10 illustrates the embodiment of a device for characterizing and detecting a sample according to the invention wherein the first lamina 28 is the bottom of a well plate or microplate 50.

The microplate 50 comprises a base 52, a support 54 having a plurality of wells 56 and a lid 58. The lid is placed on the support 54, which in turn is placed on the base 52. The lid prevents the sample 4 from evaporating, in particular the cell culture medium.

The support 54 of the microplate 50 comprises a lower extension 68. The total height of the support 54, with the lower extension 68, is larger than the height of a well 56. Thus, the lower extension 68 makes it possible to raise, for example by at least 1 mm, the bottom 60 of the wells 56 relative to the base 52 of the microplate. This available space between the bottom 60 of the wells 56 and the base 52 is intended for the imaging system 6 and the electronic controller 8.

Furthermore, the four outer corners of the lower extension 68 of the support 54 of the microplate 50 are rounded with a curve radius of 3.18±1.6 mm so that handling robots of the microplates 50 can grasp the microplate 50 by the corners.

The device also comprises a plurality of imaging systems 6 according to the invention in order to carry out parallel studies on the samples contained in the different wells 56.

In this embodiment, the first lamina 28 of each imaging system 6 is shared by all of the imaging systems placed under the support 54 of the microplate. The face 28A of the first lamina 28 intended to support the objects 5, preferably adhered cells 22, forms the bottoms 60 of the set of wells 56 of the microplate 50. The bottoms 60 are preferably flat and transparent to the light radiation transmitted by the objects 5 of the sample 4.

To that end, the first lamina 28 is made from glass or plastic and adhered under the wells 56 using a biocompatible glue, such as a class 6 USP glue used in biomedical devices, in order to form the bottom 60 of the wells 56.

Metrology markings are deposited or etched on the first lamina 28 making up the bottom 60 of the wells 56, preferably on the lower face 28B opposite the microlenses. The metrology markings are preferably 30 μm crosses with a line thickness of 4 μm, spaced apart every millimeter. These marks appear on the produced images. The metrology markings provide a reference scale for measuring the dimension of the cells and facilitating reframing of the images during image processing operations using the computer system 10.

The walls of the microplate 50 (base 52, support 54, walls of the wells 56 and lid 58) other than the bottom of the wells are made from polystyrene or polypropylene.

Furthermore, all or part of these walls are transparent to the light radiation transmitted by the objects 5 of the sample 4. In that case, the microplate 50 and the imaging systems 6 assembled under the microplate 50 are placed in a darkroom to prevent disruptions from outside light.

According to one alternative, all or part of these walls are opaque with a black or white color. In a known manner, the microplates having opaque and white walls are more particularly used for luminescence experiments.

Preferably, the walls of the microplates 50 are opaque and black in order to prevent outside light disruptions, with the exception of the first lamina 28. This first lamina 28 is transparent to the light radiation transmitted by the objects 5 of the sample, for example made from glass or plastic.

When the walls are opaque and black, it is not necessary to place the microplate 50 covered with its lid in a darkroom for imaging of the objects 5. In fact, the walls of the microplate 50 with the lid 58 act as a darkroom. Such microplates 50 are particularly suitable for fluorescence experiments.

If the lid is completely black, the light source(s) 18 are fixed on the lid 58 opposite the samples contained in the wells 56 of the microplate 50.

In the embodiment shown in FIG. 10, each imaging system 6 comprises a light source 18 that is therefore associated with a single well in order to illuminate the sample inside it.

For example, the light source 18 is a light-emitting sheet or a flat LED, such as an XLamp marketed by Cree (Durham, United States).

The light source(s) 18 can also be placed on the outer face if the lid is transparent, or if it is opaque and black with transparent windows above each well 56, so as to illuminate the inside of each well 56.

In general, light sources 18 giving off little heat are selected to limit the heating and evaporation of the sample 4.

A matrix 24 of photosensors 26 topped by a matrix 30 of optical elements is positioned under each well 56 of a microplate 50 in order to view the objects 5 disposed on the bottom 60 of each well 56 of the microplate 50, in particular so as to be able to produce an image of the sample 4, preferably cellular, in each well 56. The thickness E is then the thickness of the first lamina 28, as in the embodiment shown in FIG. 4.

Thus, several experiments are carried out and visualized at the same time in the different wells 56 of the microplate 50.

Each imaging system 6 is assembled on an electronic board 62 or printed circuit making it possible to produce the interface between the imaging systems and the electronic controller(s) 8 of the device. The electronic board 62 is shared by several imaging systems and one or more electronic controllers 8.

In a configuration of this embodiment shown in FIG. 10, the imaging systems are connected to a single electronic controller 8 by the electronic board 62, in order to centralize the interface function between the imaging systems according to the invention and the computer system 10.

The electrical trails connecting the various electronic components of the electronic board 62 are preferably buried in the printed circuit or covered with a protective varnish in order to protect them from the humid atmosphere.

The electronic board 62 is connected to the computer system 10 via an electronic port 64, connected on the board 62, and a cable 66, connect to the port on the one hand and to the computer system 10 on the other. An opening 70 is pierced in the lower extension 68 of the microplate 50 for passage of the cable 66 connecting the connection port 64 and the computer system 10.

For example, the imaging systems 6 are connected on one face of the electronic board 62 opposite the wells, the port 64 and the electronic controller 8 being on the opposite face.

According to another configuration, each imaging system 6 is connected/assembled on an electronic daughterboard connected by a connector to an electronic motherboard on which the electronic controller 8 and the connection port 64 are assembled.

The electronic board(s) 62 are secured to the microplate 50 using mechanical fastening means and bearing points disposed between the microplate 50 and the electronic board(s) 62.

In a known manner, to ensure the high transmission speed of the images to the computer system 10, the connection port 64 is a USB2, FireWire, Ethernet Gigabit or CamLink port.

According to another alternative, the two-way communications between the computer system 10 and the electronic board 62 are done by transmitters and receivers, and the power supply for the imaging system(s) 6 is done by a cell or battery close to the device.

The dimensions of the matrix 24 of photosensors 26 make it possible to cover all or only part of the bottom 60 of the well 56 opposite which it is disposed. Furthermore, the dimensions of the matrix 30 of optical elements are substantially equal to those of the matrix 24 of photosensors 26 opposite which it is disposed.

For example, each matrix 24 of photosensors 26 has an area of 3.6 mm×2.7 mm, placed under a circular well with a diameter of 9 mm.

In another example, the matrix 24 of photodetectors 26 has an area of 6.4 mm×4.6 mm placed under a well with a diameter of 18 mm.

For each imaging system 6, the center of the matrices 24 and 30 and that of a well 56 are aligned.

Using a matrix 24 of photosensors 26 and a matrix 30 of optical elements with dimensions smaller than the diameter of the well makes it possible to image the cells situated on the edge of the well whereof the behavior is often considered non-representative of the cell population.

In a known manner, the dimensions of the microplate 50 verify the primary specifications ANSI/SBS 1-2004 to 4-2004 recommended by the Society for Biomolecular Screening (SBS). More specifically, the microplates have a length of 127.76±0.5 mm and a width of 85.48±0.5 mm.

The microplates 50 have an array of 2×3, 3×4, 4×6, 6×8, 8×12, 16×24 or 32×48 wells.

The total height of the support 54 of the microplate 50 equipped with the imaging systems 6 is comprised between 14.35 mm and 35.00 mm, i.e. the distance, measured along the optical axis Z of the photosensors 26, between the end of the wells 56 opposite the end in contact with the first lamina 28 and the end of the extension 68 in contact with the base 52.

The first lamina 28 is for example a glass plate measuring 175 μm or 210 μm thick or a transparent polystyrene film measuring 125 μm thick.

The microplates 50 integrated with the imaging systems can be used inter alia for cell proliferation studies, toxicology studies, morphological analyses, motility analyses, chemotaxis analyses, viral infection analyses, cancerology studies, pharmaceutical screening analyses or research on molecules influencing cell behavior.

The electronic board 62 is 115 mm long and 75 mm wide so as to be inserted into the lower extension 68 of the support 54 of the microplate 50. Thus, no component of the electronic board touches the base 52 of the microplate 50. Furthermore, this base 52 protects the electronic board 62 from the humidity in the incubator 14.

Imaging systems according to the invention can also be disposed against the outer wall of one or more bottles in order to characterize the objects disposed on the inner wall of one or several bottles. The thickness E is then the thickness of the bottle wall.

In light of FIG. 11, a cell culture bottle 80 is equipped with an imaging system 6 according to the invention in order to monitor the proliferation of the cells in the culture bottle.

In a known manner, the culture bottle 80 is a bottle with flat walls made from polystyrene or polypropylene that preferably have a surface treatment favoring cell adhesion.

Preferably, the imaging system 6 is placed under the culture bottle 80 so as to image the objects, preferably cells 22 adhered on the lower wall 84 of the bottle 80, the lower wall 84 being the wall opposite the imaging system 6. It forms the first lamina 28 of the imaging system 6. Thus, the lower wall 84 or only part thereof has a thickness E adapted to perform cellular imaging according to the invention.

According to another alternative, the culture bottle is made from polystyrene, with the exception of all or part of the lower wall 84, which is a lamina or plate made from glass or plastic with thickness E. Said lamina, or glass or plastic plate, is adhered to the polystyrene walls of the culture bottle using a biocompatible glue such as a class 6 USP glue.

As in the embodiment shown in FIG. 10, the imaging system 6 is connected to the electronic controller 8 via an electronic board 86. An electronic port 90 connected to a cable 92 is assembled to the electronic board 86 in order to connect the electronic controller 8 to the computer system 10 of the device.

Furthermore, the electronic board 86 is secured to the lower wall 84 of the bottle 80 using mechanical fastening means 88A, 88B and bearing points disposed between the lower wall and the electronic board.

Furthermore, the light source 18 is fixed on the upper wall of the bottle 80. Furthermore, the bottle comprises a stopper 82 to prevent the sample 4 from evaporating, for example the cell culture medium.

It is possible to stack the culture bottles 80, the imaging systems 6 and the light sources 18 vertically to save space inside the incubator 14. A very flat light source such as a light-emitting sheet is then chosen to illuminate the sample of the culture bottle, which makes it easier to stack the bottles and imaging systems. If another type of light source is chosen, a space for the light source is reserved above each culture bottle using fastening means and bearing points.

The images collected by the computer system 10 can be viewed remotely using a computer server. The user accessing the images of the cells remotely may or may not decide to change the culture medium of the cells or to relocate the cells in a new culture bottle.

Microbeads with a calibrated size can be introduced into the sample so as to measure the temperature of the medium from the produced images. In fact, in a known manner, the microbeads appear on the images and the movement of a microbead between two successive images depends on the Brownian movement, i.e. the temperature. Thus, the measurement of the movement of a microbead between two successive images makes it possible to deduce the temperature by using the Stokes-Einstein equation:

$$T = \frac{3\pi r \eta \langle d^2 \rangle}{kt}$$

with r the radius of the microbead, η the viscosity of the medium, $\langle d^2 \rangle$ the distance to the square traveled by the microbead during time t, and k Boltzmann's constant (k=1, 3806504.10$^{-23}$ J.K$^{-1}$).

The precise measurement of the position of the beads on the image is done by using the metrology markings deposited or etched on the lamina 28 as previously indicated as reference, irrespective of the embodiments of the imaging system (microplate, culture bottle, etc.).

The imaging system and the associated device are intended to detect and characterize the images optically, in particular the cells.

The microlenses focus the light coming from the areas of the sample in the corresponding sensitive areas of the silicon in order to collect as much light as possible. The light intensity is integrated by each photosensor. The matrix of microlenses modifies the division (discretization) of the space done by the matrix of photosensors.

Furthermore, the first lamina 28 creates diffraction and interference effects that favor the visualization of low-contrast objects such as cells adhered to the surface of the first lamina, in particular the contour of those objects.

The field of vision of the imaging system 6 corresponds to the dimensions of the matrix 24 of photosensors 26. As an example, the field of vision is widened relative to a traditional microscope over a rectangle of several mm$^2$ and up to several cm$^2$ of area. Currently the obtained images correspond to a ×4 magnification in traditional microscopy, but over a larger field of about 3.5×4.5 mm$^2$ relative to a traditional digital opening objective. The magnification of the images differs according to the distance between the face 28A, support for the sample, of the first lamina 28 and the apex of the microlenses 34. In fact, if the sample 4 or the objects 22 are spaced away from the matrix 24 of photosensors 26, the image of the sample or of the objects is spread over an increasing number of photosensors 26.

The resolution depends on the size of the pixels, but it also depends on the focal distance of the microlenses, the distance between the sample 4 or the objects 22 and the matrix of photosensors, and the refractive index n of the medium 36.

The device has smaller dimensions, preferably that of a cube with 10 cm sides, and is easy to install in an incubator.

The reduced dimensions of the device have the advantage of the great portability of the device, while considering applications to the patient's bed, such as blood cell counting, or being able to be placed directly in an incubator while adding only the presence of a computer in the cell culture room.

The invention has been described in the context of biological applications with samples comprising cells. However, it is applicable to other fields, for example to view bacteria, yeasts, fungi, pollens, algae, liposomes, synthetic particles, and/or to detect optical responses to physicochemical phenomena such as viewing the formation of crystals in reservoirs on the first lamina 28.

The invention claimed is:

1. A system for imaging a sample including at least one cell, the system comprising:
   a sample including at least one cell,
   a matrix of photosensors, the photosensors defining an optical axis Z,
   a first lamina disposed opposite the matrix of photosensors defining a face supporting the sample, and
   a set of optical elements disposed between the matrix of photosensors and the first lamina, the set of optical elements comprising:
      a matrix of microlenses, each microlens having an apex and a refractive index, a microlens being situated above each photosensor of the matrix of photosensors, and
      an optical medium disposed between the matrix of microlenses and the first lamina, the optical medium having a refractive index, the refractive index of the optical medium being substantially between 1 and the refractive index of the microlenses,
   wherein a distance H along the optical axis of the photosensors between the face supporting the sample and the apex of each microlens is substantially between 0 and 1500 μm,
   wherein the at least one cell is covered by an arrangement comprising at least two adjacent photosensors in a first direction and two other adjacent photosensors in a second direction, the second direction being perpendicular to the first direction, the at least two adjacent photosensors being located adjacent to the at least two other photosensors said photosensors being associated with the microlenses and said at least two adjacent photosensors in a first direction and said at least two other adjacent photosensors in the second direction providing an image of the at least one cell occupying at least 2×2 pixels.

2. The imaging system according to claim 1, wherein the distance along the optical axis of the photosensors between the support face of the sample and the apex of each microlens is smaller than or equal to (−150×F×n)+(400×F), where F is the focal length of each microlens measured in the air and n the refractive index of the optical medium and the refractive index of the optical medium is substantially between 1 and 1.64.

3. The imaging system according to claim 1, comprising a light source to illuminate the sample, the light source being disposed above the sample so as to produce a transmission image.

4. The imaging system according to claim 1, comprising a light source to illuminate the sample, the light source being disposed to illuminate the sample from inside the first lamina of the imaging system perpendicularly to the optical axis of the imaging system.

5. The imaging system according to claim 3, wherein the light source has a wavelength between 200 nm and 800 nm.

6. The imaging system according to claim 5, wherein the light source is a white light.

7. The imaging system according to claim 1, wherein the optical medium is a liquid.

8. The imaging system according to claim 7, comprising a cuvette containing the liquid and the sample.

9. The imaging system according to claim 1, wherein the imaging system comprises a second lamina disposed so that the sample is situated between the first lamina and the second lamina.

10. The imaging system according to claim 1, wherein the support face of the sample of the first lamina is disposed opposite the matrix of photosensors.

11. The imaging system according to claim 1, wherein the first lamina includes a slide and a removable lamina, the removable lamina being alongside the slide and the removable lamina defining the support face of the sample.

12. The imaging system according to claim 1, wherein the imaging system comprises a means for adjusting the distance, measured along the optical axis of the photosensors, between the support surface of the sample and the apex of the microlenses.

13. The imaging system according to claim 1, wherein the first lamina comprises a plurality of microchambers or microchannels.

14. The imaging system according to claim 1, wherein the photosensors can detect a light emitted between 200 nm and 800 nm produced by bioluminescense, chemiluminescense or fluorescence.

15. The imaging system according to claim 1, wherein the opening diameter of each microlens is substantially comprised between 0.7 and 10 μm.

16. A device for detecting and characterizing a sample, the device comprising an imaging system according to claim 1, an electronic controller configured to steer the imaging system and a computer system configured to control the imaging system.

17. The device according to claim 16, comprising an incubation chamber in which the imaging system and the sample are placed.

18. A device for detecting and characterizing a sample, the device comprising at least two imaging systems according to claim 1, an electronic controller configured to steer the imaging system and a computer system configured to control the imaging system, wherein the imaging systems are steered in parallel by the electronic controller.

19. The device according to claim 18, wherein the first lamina is shared by at least two adjacent imaging systems.

* * * * *